(12) United States Patent
Missos

(10) Patent No.: US 8,574,296 B2
(45) Date of Patent: Nov. 5, 2013

(54) DUAL TENDON BUNDLE

(75) Inventor: Nicholas Missos, Winona Lake, IN (US)

(73) Assignee: Biomet Manufacturing Corporation, Warsaw, IN (US)

( * ) Notice: Subject to any disclaimer, the term of this patent is extended or adjusted under 35 U.S.C. 154(b) by 179 days.

(21) Appl. No.: 13/077,079

(22) Filed: Mar. 31, 2011

(65) Prior Publication Data

US 2012/0253465 A1  Oct. 4, 2012

(51) Int. Cl.
*A61F 2/08* (2006.01)

(52) U.S. Cl.
USPC ........................................... 623/13.11

(58) Field of Classification Search
USPC ................................ 623/13.11–13.2
See application file for complete search history.

(56) References Cited

U.S. PATENT DOCUMENTS

| | | | |
|---|---|---|---|
| 4,942,875 A * | 7/1990 | Hlavacek et al. | 606/230 |
| 5,026,398 A * | 6/1991 | May et al. | 623/13.11 |
| 5,281,422 A * | 1/1994 | Badylak et al. | 623/13.11 |
| 5,298,012 A | 3/1994 | Handlos | |
| 7,195,642 B2 | 3/2007 | McKernan et al. | |
| 8,202,318 B2 * | 6/2012 | Willobee | 623/13.14 |
| 2001/0018619 A1 | 8/2001 | Enzerink et al. | |
| 2005/0209542 A1 | 9/2005 | Jacobs et al. | |
| 2006/0229722 A1 * | 10/2006 | Bianchi et al. | 623/13.14 |
| 2007/0239275 A1 | 10/2007 | Willobee | |
| 2007/0250163 A1 * | 10/2007 | Cassani | 623/13.17 |
| 2008/0234819 A1 | 9/2008 | Schmieding et al. | |
| 2009/0069893 A1 | 3/2009 | Paukshto et al. | |
| 2009/0287308 A1 * | 11/2009 | Davis et al. | 623/13.12 |
| 2010/0049319 A1 | 2/2010 | Dougherty | |
| 2010/0298937 A1 * | 11/2010 | Laurencin et al. | 623/13.14 |
| 2012/0059468 A1 * | 3/2012 | Mattern et al. | 623/13.14 |
| 2012/0179253 A1 * | 7/2012 | Altman et al. | 623/13.11 |
| 2012/0221104 A1 * | 8/2012 | Altman et al. | 623/8 |
| 2012/0253464 A1 * | 10/2012 | Hwang et al. | 623/13.18 |

FOREIGN PATENT DOCUMENTS

| | | |
|---|---|---|
| FR | 2 697 151 A1 | 4/1994 |
| GB | 2 276 823 A | 10/1994 |
| GB | 2 342 865 A | 4/2000 |
| WO | WO-2008/116127 A2 | 9/2008 |

OTHER PUBLICATIONS

International Search Report and Written Opinion Issued in the International Application PCT/US2012/030303.
Tsuda, E., et al., "Comparable Results between Lateralized Single- and Double-Bundle ACL Reconstructions," Clin. Orthop. Relat. Res., 2009, 467(4): 1042-1055.

(Continued)

*Primary Examiner* — Suzette J Gherbi
(74) *Attorney, Agent, or Firm* — Novak Druce Connolly Bove + Quigg LLP

(57) ABSTRACT

The present invention relates generally to methods for preparing a dual tendon bundle that is useful as a replacement ligament or tendon graft for, for example, anterior cruciate ligament (ACL) reconstruction. More particularly, the dual tendon bundle prepared according to the present invention has a functional cross section diameter and/or a minimum length that meets or exceeds the standard requirements for replacement ligament or tendon grafts. The present invention further relates to the dual tendon bundle prepared by the disclosed methods and packages comprising the same. Methods of using the dual tendon bundle prepared according to the present invention by providing the dual tendon bundle thus obtained for implanting into a patient in need thereof are also provided.

10 Claims, 5 Drawing Sheets

(56) References Cited

OTHER PUBLICATIONS

Li, B., et al., "Arthroscopic Single-Bundle Posterior Cruciate Ligament Reconstruction: Retrospective Review of Hamstring Tendon Graft Versus LARS Artificial Ligament," Int. Orthop., 2009, 33(4): 991-996.

Trojani, C., et al., "Four-Strand Hamstring Tendon Autograft for ACL Reconstruction in Patients Aged 50 Years or Older," Orthop. Traumatol. Surg. Res., 2009, 95(1): 22-27.

* cited by examiner

DUAL TENDON BUNDLE

FILED OF THE INVENTION

The present invention relates generally to methods for preparing a dual tendon bundle that is useful as a replacement ligament or tendon graft for, for example, anterior cruciate ligament (ACL) reconstruction. More particularly, the dual tendon bundle prepared according to the present invention has a functional cross section diameter and/or a minimum length that meets or exceeds the standard requirements for replacement ligament or tendon grafts. The present invention further relates to the dual tendon bundle prepared by the disclosed methods and packages comprising the same. Methods of using the dual tendon bundle prepared according to the present invention by providing the dual tendon bundle thus obtained for implanting into a patient in need thereof are also provided.

BACKGROUND OF THE INVENTION

The complete or partial detachment of ligaments, tendons and/or other soft tissues from their associated bones within the body are relatively common injuries. Tissue detachment may occur as the result of an accident such as a fall, overexertion during a work-related activity, during the course of an athletic event, or in any one of many other situations and/or activities. Such injuries are generally the result of excess stress being placed on the tissues.

Partial detachment of a ligament or a tendon, generally referred to "sprain," usually heals itself if given sufficient time with care to avoid further exposing the injury to undue stress during the healing process. However, when a ligament or tendon is completely detached from its associated bone or bones, or if it is severed as the result of a traumatic injury, partial or permanent disability may result. A number of surgical procedures are thus developed for re-attaching such detached tissues and/or completely replacing severely damaged tissues. In the case where complete replacement is required due to the significant damage to the ligament or tendon, a replacement ligament or tendon graft is needed for such surgical procedures.

Replacement ligament or tendon grafts often involve autografts, for which suitable ligament or tendon graft material is harvested from elsewhere in the patient's body. However, patients often experience considerable pain at the donor site following harvest of the graft material. To avoid additional injury and pain and suffering sustained by the patient, and also to facilitate the recovery process, allografts, such as grafts from a corpse, may be used as replacement ligament or tendon grafts.

In order to be used as an implanting graft, a replacement ligament or tendon graft must meet certain requirements. For example, a replacement ligament or tendon graft typically has a functional cross section diameter greater than 8 mm and a minimum length of about 200 mm. When a graft material does not meet these requirements, it cannot be used and has to be discarded.

It is known in the art to double, triple, or even quadruple the thickness of a tendon graft to produce a replacement graft that has a strength similar to the ligament intended to replace. To do so, a surgeon would usually loop the graft material after it is harvested and suture opposing lengths of the graft material together. See e.g., U.S. Pat. No. 5,298,012 and U.S. Patent Application Publication No. 2007/0250163. Because the folding of the harvested graft material necessarily reduces the length of the resulting replacement graft, only graft materials with sufficient length may be used.

Similarly, to provide a replacement ligament or tendon graft with uniform cross-section thickness, U.S. Pat. No. 7,195,642 discloses folding the two end portions of a harvested tendon graft material, which are thinner than the midsection portion, towards the midsection portion, and suturing them to the adjacent end of the midsection portion to form a double-folded replacement ligament or tendon graft. Such a double-folded ligament or tendon graft may provide a uniform cross-section thickness that would likely meet the functional cross section diameter requirement. However, like the single folding of the graft material described above, because the double folding of the two end portions unavoidably reduces the length of the resulting graft, only graft materials with sufficient length may be used.

Alternatively, a replacement ligament or tendon graft may also be obtained by using a plurality of single tendon strands and placing them together so that at least a portion of one tendon strand is adjacent to a portion of another tendon strand by suture. As such, the replacement ligament or tendon graft thus obtained has at least two regions, one region formed of at least a plurality of tendon strands tied together, and the other region formed of loose segments of the plurality of tendon strands. See e.g., U.S. Patent Application Publication No. 2007/0239275.

In view of the limiting supply of ligament or tendon allograft materials, and because when a graft material does not meet the necessary requirements for implant, it cannot be used and has to be discarded, there still exists a need to provide a means to produce replacement ligament or tendon grafts while making the maximum use of every possible graft material that becomes available.

SUMMARY OF THE INVENTION

The present invention provides a method for preparing a dual tendon bundle that is useful as a replacement ligament or tendon graft.

In one aspect, the invention provides a method for preparing a dual tendon bundle comprising:
(i) cutting a first tendon graft and a second tendon graft to matching length, each of the first tendon graft and the second tendon graft comprises a head end and a tail end with the head end being wider than the tail end;
(ii) placing the first tendon graft on top of the second tendon graft in such way that the head end of the first tendon graft is together with the tail end of the second tendon graft and the head end of the second tendon graft is together with the tail end of the first tendon graft; and
(iii) wrapping the head end of the first tendon graft around the tail end of the second tendon graft and wrapping the head end of the second tendon graft around the tail end of the first tendon graft.

Optionally, the method further comprises securing the wrapping of the head end of the first tendon around the tail end of the second tendon graft and the wrapping of the head end of the second tendon around the tail end of the first tendon graft with a securing device. In one embodiment, the securing device is a suture. In another embodiment, the securing device is tubular clip.

In yet another embodiment, the method further comprises measuring the functional cross section diameter of the dual tendon bundle thus prepared.

In a further embodiment, the method further comprises packaging the dual tendon bundle thus prepared in a container. Preferably, the container is sterilized. In another preferred embodiment, the method further comprises providing a label outside of the container providing at least the functional cross section diameter of the dual tendon bundle.

In another aspect, the invention provides a dual tendon bundle useful as a replacement ligament or tendon graft.

In one embodiment, the dual tendon bundle comprises a first tendon graft and a second tendon graft, each of the first tendon graft and the second tendon graft comprises a head end and a tail end with the head end being wider than the tail end, wherein the first tendon graft is placed on top of the second tendon graft in such way that the head end of the first tendon graft is together with the tail end of the second tendon graft and the head end of the second tendon graft is together with the tail end of the first tendon graft, and wherein the head end of the first tendon graft is wrapped around—the tail end of the second tendon graft and the head end of the second tendon graft is wrapped around the tail end of the first tendon graft.

Optionally, the wrapping of the head end of the first tendon around the tail end of the second tendon graft and the wrapping of the head end of the second tendon around the tail end of the first tendon graft is secured by a securing device. In one embodiment, the securing device is a suture. In another embodiment, the securing device is tubular clip.

Preferably, any of the aforementioned dual tendon bundles has a functional cross section diameter of greater than 8 mm. In another preferred embodiments, any of the aforementioned dual tendon bundles has a minimum length of about 200 mm.

In yet another aspect, the invention provides a container comprising any of the aforementioned dual tendon bundles. Preferably, the container is sterilized. In another preferred embodiments, the container further comprises a label outside of the container providing at least the functional cross section diameter of the dual tendon bundle.

In a further aspect, the invention provides a package comprising any of the aforementioned dual tendon bundles or a container comprising any of the aforementioned dual tendon bundles. Preferably, the package further comprises a label providing at least the functional cross section diameter of the dual tendon bundle contained therein.

In a yet further aspect, the invention provides a method of providing a ligament or a tendon to a medical professional for implanting into a patient in need thereof, comprising:

(i) obtaining a dual tendon bundle according to any of the aforementioned methods or obtaining any of the aforementioned dual tendon bundles, and (ii) providing the dual tendon bundle to a medical professional for implanting into a patient in need thereof.

Optionally, the wrapping of the dual tendon bundle used for implanting is secured by a securing device, and such a securing device is removed after the dual tendon bundle is implanted into the patient. In one embodiment, the securing device is a suture. In another embodiment, the securing device is tubular clip.

The methods and compositions of the present disclosure provide benefits over methods and compositions among those known in the art. Such benefits can include, but are not limited to, affording ligament or tendon graft materials to meet certain requirements in order to be used as replacement ligament or tendon grafts. Further areas of applicability will become apparent from the detailed description provided hereinafter. It should be understood that the Detailed Description and specific examples, while indicating preferred embodiments of the present disclosure, are intended for purposes of illustration only and not intended to limit the scope of the present disclosure.

BRIEF DESCRIPTION OF THE DRAWINGS

The present disclosure will become more fully understood from the detailed description and the accompanying drawings, wherein.

DETAILED DESCRIPTION OF THE PREFERRED EMBODIMENTS

The following description of the embodiment(s) is merely exemplary in nature and is in no way intended to limit the invention, its applications, or uses.

Throughout this application, various publications are referenced. The citation of references does not constitute an admission that those references are prior art or have any relevance to the patentability of the disclosure provided herein. Any discussion of the content of references cited in the present disclosure is intended merely to provide a general summary of assertions made by the authors of the references, and does not constitute an admission as to the accuracy of the content of such references. The disclosures of all of these publications and those references cited within those publications are hereby incorporated by reference in their entireties into this application in order to more fully describe the state of the art to which this invention pertains. The terminology used herein is for the purpose of describing specific embodiments only and is not intended to be limiting. As used herein, "a" or "an" can mean one or more, depending upon the context in which it is used. Thus, for example, reference to "a tendon graft" can mean that at least one tendon graft can be used. When the term "about" is used in conjunction with a numerical range, it modifies that range by extending the boundaries above and below the numerical values set forth. In general, the term "about" is used herein to modify a numerical value above and below the stated value by a variance of 20%, preferably 10% up or down (higher or lower). The word "comprise," "comprising," "include," "including," and "includes" as used herein and in the following claims is intended to specify the presence of one or more stated features, integers, components, or steps, but they do not preclude the presence or addition of one or more other features, integers, components, steps, or groups thereof.

In one aspect, the invention provides a dual tendon bundle that is useful as a replacement ligament or tendon graft. As such, the materials to be used to prepare the dual tendon bundle according to the present disclosure must be biocompatible. As used herein, such a "biocompatible" component is one that is suitable for use with humans and/or animals without undue adverse side effects (such as toxicity, irritation, and allergic response) commensurate with a reasonable benefit/risk ratio.

Figure 1:
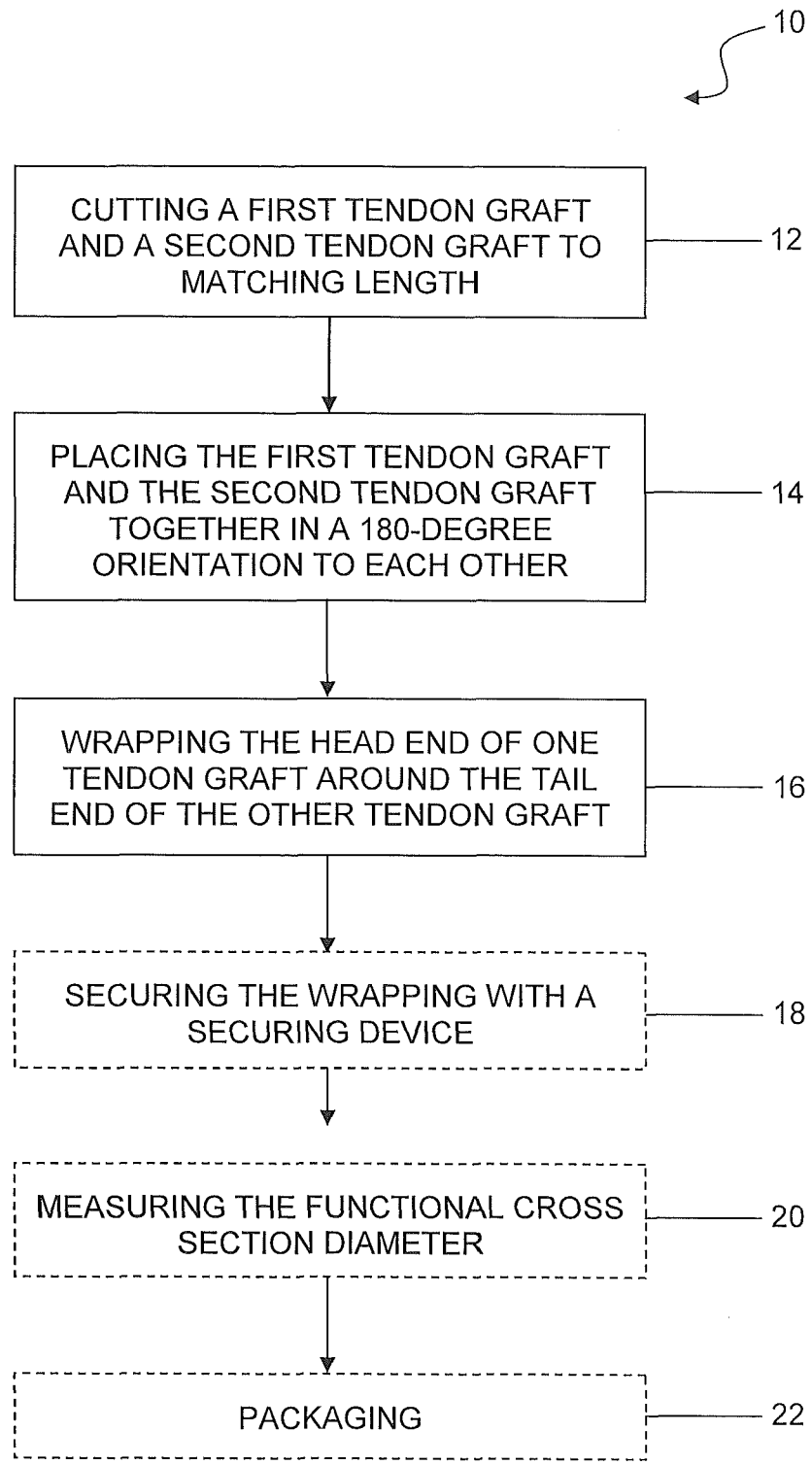
FIG. 1 depicts a flow chart illustrating an exemplary method according to the invention.

Referring now to FIG. 1, a flowchart 10 which illustrates embodiments of the methods according to the present disclosure for preparing a dual tendon bundle. In a first step 12, two pieces of tendon graft (i.e. a first tendon graft and a second tendon graft) are cut to matching length.

Tendon grafts used according to the present disclosure may be obtained from a variety of sources including allograft, xenograft, or synthetic material. If allograft or xenograft material is used, it may be prepared by removing extraneous tissue using any standard protocol. In preferred embodiments, the tendon graft is obtained from allograft material, such as from a corpse. Tendon graft may be obtained from different areas such as a patellar tendon, a hamstring tendon, an Achilles tendon, or a peroneous tendon. The tendon graft may also be obtained from tissue banks, such as LifeLink, Tampa, Fla.

The tendon graft thus obtained is then cut to a proper size for assembling into a dual tendon bundle according to the methods described in the present disclosure. Typically, the tendon graft is cut to a length ranging from about 180 mm to about 350 mm. However, the maximum length of the tendon graft is generally not a limiting factor because of the natural limitation on the length of tendons. In some preferred embodiments, the tendon graft is cut to a minimum length of about 180 mm. In other preferred embodiments, the tendon graft is cut to a minimum length of about 200 mm. However, it should be noted that, while preferred lengths are disclosed, these lengths are merely typical of lengths needed, but other lengths of grafts are also within the scope of the invention.

Figure 2:
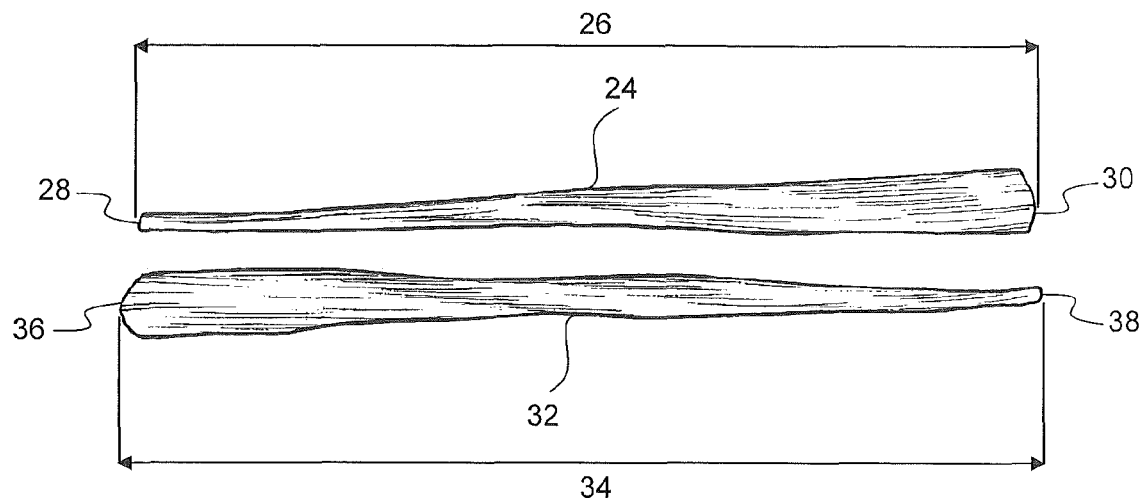
FIG. 2 depicts two tendon grafts that are cut to matching length and placed in such way according to the present disclosure.

Referring now to FIG. 2, which is a perspective view of two pieces of tendon graft 24, 32 that are cut to matching length 26, 34. Tendons are tough band of fibrous connective tissue that typically has a wide section that tapers to a narrow section. As used herein, the wider section of a tendon graft is referred to as the "head end" and the narrower section is referred to as the "tail end" of the tendon graft. As illustrated in FIG. 2, the tendon graft 24 has a head end 30 and a tail end 28, and the tendon graft 32 has a head end 36 and a tail end 38. Both tendon grafts 24, 32 are cut to matching length 26, 34.

Reference is now made again to FIG. 1. After obtaining two pieces of tendon graft and cutting them to matching length (step 12), these two pieces of tendon graft are placed together in an orientation that is 180 degree to each other (step 14). As such, the head end of the first tendon graft is together with the tail end of the second tendon graft and the head end of the second tendon graft is together with the tail end of the first tendon graft as illustrated in FIG. 2.

As can be seen in FIG. 2, the first tendon graft 24 is placed in an orientation that is 180 degree to the second tendon graft 32. Because the two tendon grafts 24, 32 are cut to matching length, the placement of these two tendon grafts in a 180-degree orientation to each other aligns the head end 30 of the first tendon graft 24 with the tail end 38 of the second tendon graft 32, and the tail end 28 of the first tendon graft 24 with the head end 36 of the second tendon graft 32.

Referring now again to FIG. 1, after obtaining two pieces of tendon graft and placing them together as described above (steps 12 and 14), the head end of each tendon graft is then wrapped around the tail end of the corresponding tendon graft (step 16). This wrapping continues along the entire length of the combined tendons, thus creates a dual tendon bundle that has a consistent cross section along the entire length of the bundle.

Figure 3:
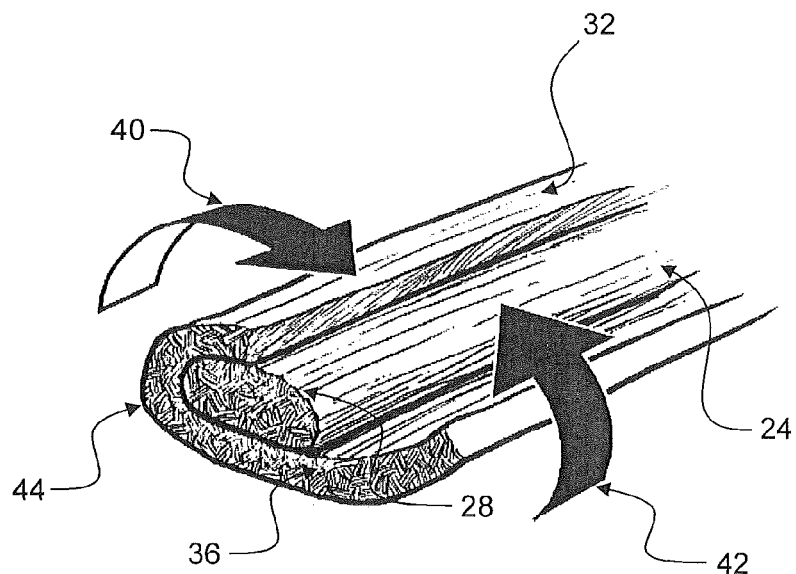
FIG. 3 depicts wrapping the head end of one tendon graft around the tail end of the other tendon graft according to a method of the invention.

Reference is now made to FIG. 3, which is a perspective view of the aforementioned wrapping step. As can be seen in FIG. 3, the tail end 28 of the tendon graft 24 is wrapped around by the head end 36 of the tendon graft 32 in a direction shown by arrows 40, 42. Such a wrapping results in a combined tendon end 44 that consists of a head end of one tendon graft and a tail end of the other tendon graft. Though not illustrated in the drawings, a similar wrapping occurs in the opposite end of the tendon grafts, where the tail end 38 of the tendon graft 32 is wrapped around by the head end 30 of the tendon graft 24.

Referring once again to FIG. 1, after cutting two tendon grafts to matching length (step 12) and placing them together (step 14), followed by wrapping them with one another (step 16), the aforementioned wrapping of the tail end of one tendon graft by the head end of the corresponding tendon graft may be optionally secured with a securing device (step 18). A "securing device" as used herein refers to any means that can hold tissues together. Examples of such a securing device include, but not limited to, a suture, a tubular clip, or a ZIPLOOP™ (Biomet Sports Medicine, Warsaw, Ind.).

Figure 4A:
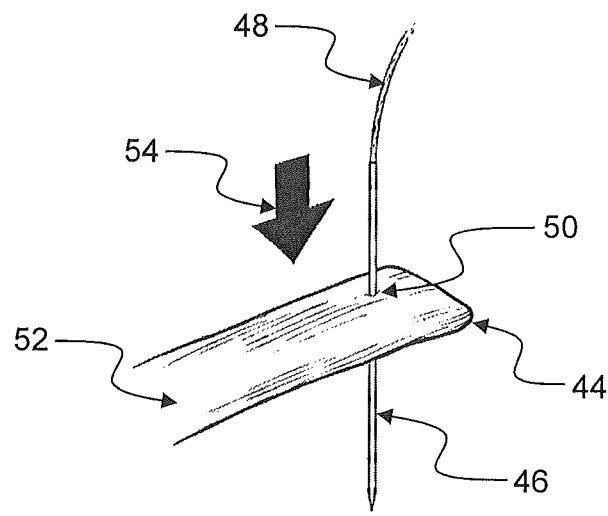
FIG. 4A-4E depicts securing the wrapping of the combined tendon bundle by a suture.
Figure 4B:
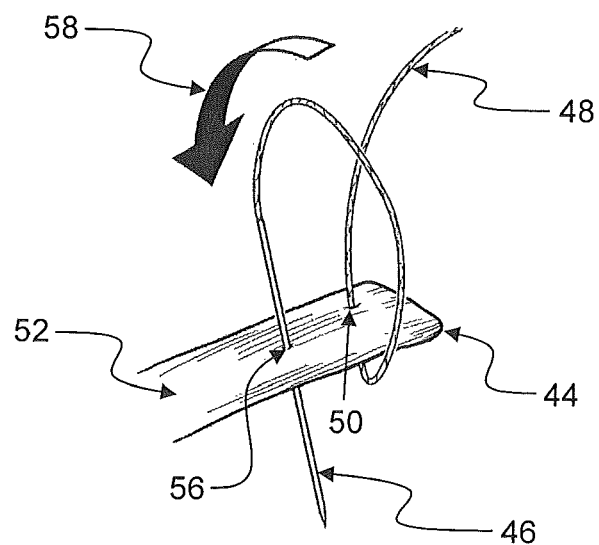
Figure 4C:
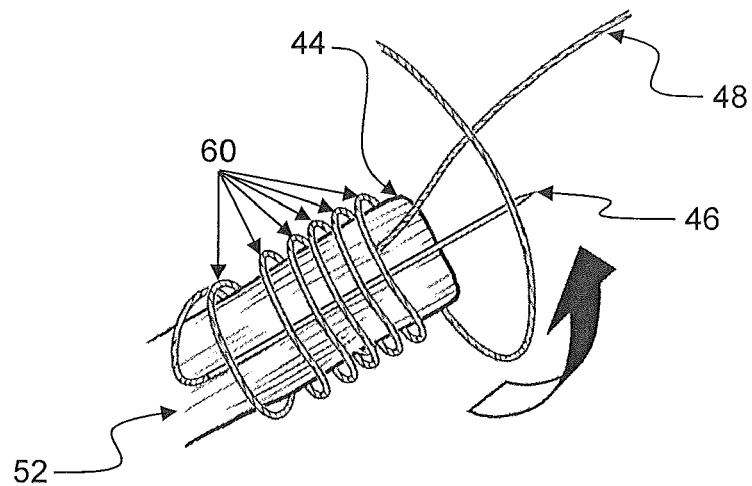
Figure 4D:
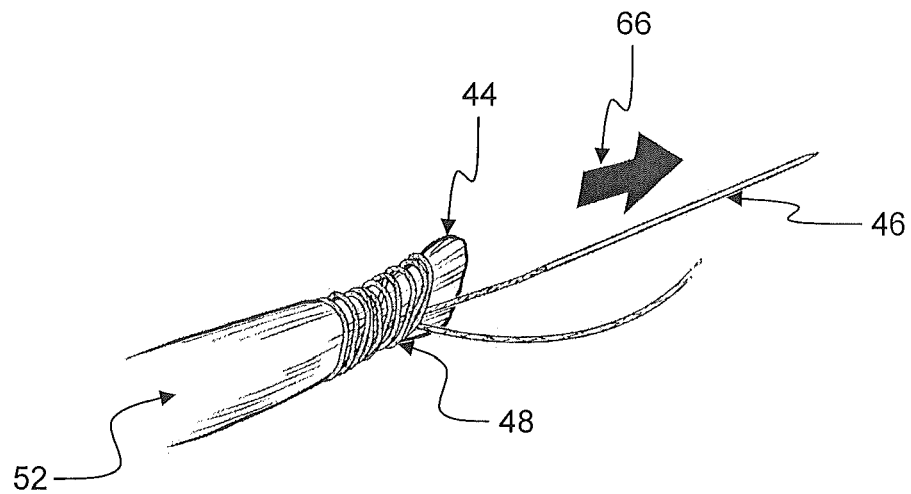
Figure 4E:
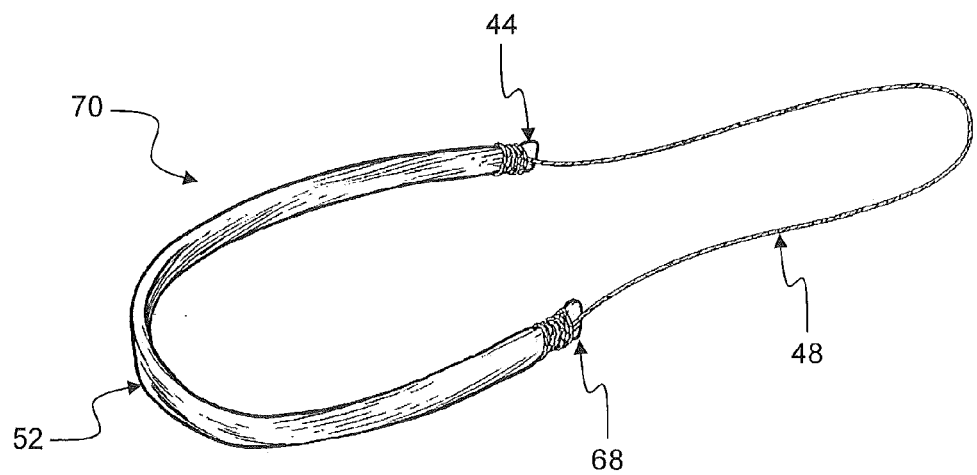

An example of securing the wrapping by a suture is shown in FIG. 4A-4E. Subsequent to the wrapping step, the combined tendon end 44 thus obtained is secured by a suture 48. According to an exemplary embodiment, a free floating thin needle 46 attached to a suture 48 is passed from top down through the combined tendon end 44 at a first location 50 close to the end of the combined tendon bundle 52 in a direction shown by arrow 54 (FIG. 4A). Sweeping over to the top, the free floating thin needle 46 is once again passed from top down through the combined tendon end 44 at a second location 56 closer to the center of the combined tendon bundle 52 as compared to the first location 50 in the same direction shown by arrow 58 (FIG. 4B). Again sweeping over to the top, the free floating thin needle 46 is then placed on the same side from which it passed through the combined tendon bundle 52 (i.e. top side) and wrapped several times 60 with suture 48 passed through the tendon (FIG. 4C). The wrapping of the combined tendon end 44 by the suture 48 is then tied up by pulling the floating thin needle 46 towards the opposite direction of the combined tendon 52 shown by arrow 66 (FIG. 4D). As such, the combined tendon end 44 is secured by the suture 48. The same technique may be used to secure the opposite end of the combined tendon bundle. In some embodiments, both ends 44, 68 of the combined tendon bundle 52 may be secured by the same suture 48, thus creates an end product 70 as illustrated in FIG. 4E.

Although FIG. 4A-4E illustrate securing the wrapping at the combined tendon end with a suture, as mentioned above, the invention is not limited to this exemplary embodiment and encompasses embodiments wherein the wrapping at the combined tendon end is secured by other equivalent means. Moreover, it should be noted that the use of a securing device to hold the wrapping of the tail end of one tendon graft by the head end of the corresponding tendon graft is only optional and if it is used, is temporary. Thus, if a securing device is used, such a securing device is removed when the dual tendon bundle thus obtained is implanted into a patient in need thereof.

Referring now once again to FIG. 1, following steps 12, 14, and 16, the dual tendon bundle thus obtained may be optionally subjected to measurement of its functional cross section diameter (step 20). This measuring step may be performed with or without the wrapping being secured with a securing device (step 18). Standard protocols known in the art for measuring functional cross section diameter of a tendon graft may be used. As a non-limiting example, the functional cross section diameter of a tendon graft may be measured by doubling the tendon graft and looping it over a suture, thus created a ligament construct with a looped end and a ligament end which consists of both ends of the tendon graft. The suture is then passed through gage holes of various sizes and the trailing ligament construct is pulled through the holes. When a strong resistance is felt in pulling the trailing ligament construct through a gage hole, the size of such a gage hole determines the functional cross section diameter of the tendon graft measured.

In preferred embodiments, the dual tendon bundle thus obtained may have a functional cross section diameter ranging from about 7 mm to about 14 mm. In some preferred embodiments, the dual tendon bundle thus obtained may have a functional cross section diameter of greater than 8 mm. In other preferred embodiment, the dual tendon bundle thus obtained may have a functional cross section diameter of greater than 10 mm. However, it should be noted that, while preferred functional cross section diameters are disclosed, they are merely typical of functional cross section diameters needed, but other functional cross section diameters of grafts are also within the scope of the invention.

Upon completion of the preparation according to the aforementioned methods, the dual tendon bundle thus obtained may optionally be further packaged in a container. A "container" as used herein refers to any means that may be used to contain, store, and/or transport the dual tendon bundle after preparation and before use. Examples of such a container include, but not limited to, bags, boxes, bottles, or cans. In preferred embodiments, the container used is sterilized. Standard protocols known in the art for sterilization, such as irradiation or chemical sterilization techniques, may be used to sterilize the container. In other preferred embodiments, outside of the container may further comprise a label that provides information related to the dual tendon bundle packaged within the container. Examples of such information include, but not limited to, the length and the functional cross section diameter of the dual tendon bundle and other information that may be material to the use and application of the dual tendon bundle contained. In yet other preferred embodiments, the dual tendon bundles obtained according to the aforementioned methods, or the aforementioned containers containing the dual tendon bundles thus obtained, may be further included in a package or a kit together with other components, such as materials needed for implant. Such a package or a kit may further include a label providing information related to the dual tendon bundle contained in the package or the kit and information as to the use and handling thereof.

The dual tendon bundle according to the present disclosure may be used as a replacement ligament or tendon graft for ligament or tendon replacement or reconstruction. Accordingly, in another aspect, the present disclosure provides a method of providing a ligament or a tendon to a medical professional for implanting into a patient in need thereof, such a method comprises (i) obtaining a dual tendon bundle according to the present disclosure, and (ii) providing the dual tendon bundle to a medical professional for implanting into a patient in need thereof. Methods known in the art for implanting a ligament or tendon into a patient in need thereof may be used. Typically, a replacement ligament or tendon graft of appropriate size is selected and inserted in pre-drilled holes, such as femoral and tibial holes in the case of anterior cruciate ligament replacement. After insertion, the graft can be fixed in place using fixation devices including interference screws, cross-pins, tab-loop anchors, and screws and washers.

For instance, the dual tendon bundle of the present disclosure may be used as an anterior cruciate ligament (ACL) graft in anterior cruciate ligament reconstruction. In this procedure, the injured or torn ligament is removed from the knee and the graft is inserted through a hole or holes created by a boring tool. Methods for performing such a procedure are well established in the art and routinely used by skilled surgeons. Examples of applicable procedures include, but not limited to, single tunnel single bundle anterior cruciate ligament reconstruction (STBDACLR) and double bundle double tunnel anterior cruciate ligament reconstruction (DB-DTACLR), a brief description of which is provided in U.S. Patent Application Publication No. 2010/0049319, single tunnel double bundle anterior cruciate ligament reconstruction (STBDACLR) as described in U.S. Patent Application Publication No. 2010/0049319, and all-inside double bundle anterior cruciate ligament reconstruction as described in U.S. Patent Application Publication No. 2008/0234819. The disclosure of the aforementioned documents is hereby incorporated by reference herein in its entirety. Once the dual tendon bundle graft is implanted and fixed in place, the securing device, such as a suture, a tubular clip, or a ZIPLOOP™, if used, is then removed.

While the invention has been described in detail and with reference to various embodiments thereof, it will be apparent to those skilled in the art that various changes and modifications can be made therein and equivalents may be substituted for elements thereof without departing from the spirit and scope of the invention as defined in the claims. Furthermore, the mixing and matching of features, elements and/or functions between various embodiments is expressly contemplated herein so that one of ordinary skill in the art would appreciate from this disclosure that features, elements and/or functions of one embodiment may be incorporated into another embodiment as appropriate, unless described otherwise above.

What is claimed is:

1. A dual tendon bundle comprising a first tendon graft and a second tendon graft, each of the first tendon graft and the second tendon graft comprises a head end and a tail end with the head end being wider than the tail end, wherein the first tendon graft is placed on top of the second tendon graft in such way that the head end of the first tendon graft is together with the tail end of the second tendon graft and the head end of the second tendon graft is together with the tail end of the first tendon graft, and wherein the head end of the first tendon graft is wrapped around the tail end of the second tendon graft and the head end of the second tendon graft is wrapped around the tail end of the first tendon graft.

2. The dual tendon bundle of claim 1, wherein the wrapping of the head end of the first tendon around the tail end of the second tendon graft and the wrapping of the head end of the second tendon around the tail end of the first tendon graft is secured by a securing device.

3. The dual tendon bundle of claim 2, wherein the securing device is a suture or a tubular clip.

4. The dual tendon bundle of claim 1, having a functional cross section diameter of 8 mm or greater.

5. The dual tendon bundle of claim 1, having a minimum length of about 200 mM.

6. A sterile container comprising the dual tendon bundle of claim 1.

7. The sterile container of claim 6, further comprising a label outside of the sterile container providing at least the functional cross section diameter of the dual tendon bundle.

8. A package comprising the dual tendon bundle of claim 1 or a sterile container comprising said dual tendon bundle.

9. The package of claim 8, further comprising a label providing at least the functional cross section diameter of the dual tendon bundle.

10. The dual tendon bundle of claim 1, wherein the first tendon graft and/or the second tendon graft are obtained from a patellar tendon, a hamstring tendon, an Achilles tendon, or a peroneous tendon.

* * * * *